United States Patent [19]

Daikuzono

[11] Patent Number: 5,496,307
[45] Date of Patent: Mar. 5, 1996

[54] LASER LIGHT IRRADIATION APPARATUS FOR MEDICAL TREATMENT

[75] Inventor: Norio Daikuzono, Chiba, Japan

[73] Assignee: S.L.T. Japan Co., Ltd., Tokyo, Japan

[21] Appl. No.: 118,827

[22] Filed: Sep. 10, 1993

[51] Int. Cl.⁶ .................................................. A61B 17/36
[52] U.S. Cl. .................... 606/15; 606/7; 606/17
[58] Field of Search ........................... 606/7–18; 607/89

[56] References Cited

U.S. PATENT DOCUMENTS

| | | | |
|---|---|---|---|
| 4,608,980 | 9/1986 | Aihara | 606/16 |
| 4,672,961 | 6/1987 | Dawes. | |
| 4,736,743 | 4/1988 | Daikuzono. | |
| 4,785,815 | 11/1988 | Cohen | 606/7 |
| 4,832,024 | 5/1989 | Boussignac | 606/7 |
| 5,163,935 | 11/1992 | Black et al. | 606/7 |
| 5,192,278 | 3/1993 | Hayes et al. | 606/7 |
| 5,242,438 | 9/1993 | Saadatmanesh et al. | 606/15 |
| 5,246,436 | 9/1993 | Rowe | 606/16 |
| 5,370,649 | 12/1994 | Gardetto et al. | 606/7 |
| 5,380,317 | 1/1995 | Everett et al. | 606/15 |

Primary Examiner—Stephen C. Pellegrino
Assistant Examiner—Michael Peffley
Attorney, Agent, or Firm—Lowe, Price, LeBlanc & Becker

[57] ABSTRACT

A laser light irradiation apparatus for medical treatment by irradiating an object tissue with laser lights transmitted through an optical fiber or fibers comprises a laser light reflector provided in front of the laser light emitting end of said optical fiber for reflecting the laser lights in a lateral direction of the apparatus, a covering which covers the reflector and is capable of transmitting the laser lights at least at the side portion thereof, wherein fluid is continuously supplied to a space between the covering and said reflector.

5 Claims, 2 Drawing Sheets

5,496,307

LASER LIGHT IRRADIATION APPARATUS FOR MEDICAL TREATMENT

BACKGROUND OF THE INVENTION

1. Field of the Invention

The present invention relates to a laser light irradiation apparatus and in particular to a laser light irradiation apparatus for conducting a medical treatment such as heating, vaporization and incision of a living tissue by irradiating it with laser lights.

2. Description of Prior Art

Recently, the laser light treatment by irradiating an object tissue with laser lights for heating and/or vaporizing the tissue has been widely adopted. Such treatment relying on irradiation with the laser lights has an advantage in that damage to the tissue and bleeding is less.

A contact type laser probe is disclosed in U.S. Pat. No. 4,736,743 issued to the present inventor. With this laser probe, laser lights are emitted forward mainly from the front end of the probe.

In a body cavity such as stomach and blood vessel, it may be necessary to selectively irradiate the area in the cavity with the laser lights to prevent no irradiated area in the cavity from being thermally damaged with the laser lights.

In order to prevent such damage to the tissue, means for inserting a catheter into a blood vessel and for reflecting the laser lights at the head is provided in the U.S. Pat. No. 4,672,961.

If foreign material from tissue is deposited on the laser light reflecting surface when such type of laser light irradiation apparatus is used, the reflecting surface would be excessively heated on exposure to the laser lights and might be burnt. Accordingly, it is necessary to emit the laser lights at a low power. If the blood flows into the front end portion of the optical fiber or a foreign material is deposited thereon, the front end portion of the optical fiber might be excessively heated and the power of the emitted laser lights become insufficient.

SUMMARY OF THE INVENTION

Therefore, it is an object of the present invention to provide a laser light irradiation apparatus for medical treatment which is capable of preventing damage to an optical fiber or a reflector by preventing the inclusion of a foreign material such as tissue and by cooling the emitting end portion of the optical fiber and the reflecting surface even if the laser lights are emitted at a high power.

In order to accomplish the above-mentioned object, the present invention provides a laser light irradiation apparatus for medical treatment by irradiating an object tissue with laser lights transmitted through an optical fiber or fibers, comprising a laser light reflector provided in front of the laser light emitting end of said optical fiber for reflecting the laser lights in a lateral direction of the apparatus; a covering which covers the reflector and is capable of transmitting the laser lights at least at the side portion thereof; and means for continuously supplying fluid to a space between the covering and said reflector.

Said reflector may be linked with the front end of the optical fiber, said reflector being formed with an opening on the side thereof, said opening having a slanted surface which intersects with the emitted laser light.

A protection tube may be provided to surround said optical fiber, said protection tube being linked with said covering, said covering being formed with a fluid outlet through which the supplied fluid having passed through said protection tube can be discharged.

DESCRIPTION OF PREFERRED EMBODIMENTS

The present invention will become more apparent by reading the following description of preferred embodiments with reference to the drawings.

Figures 1, 2:
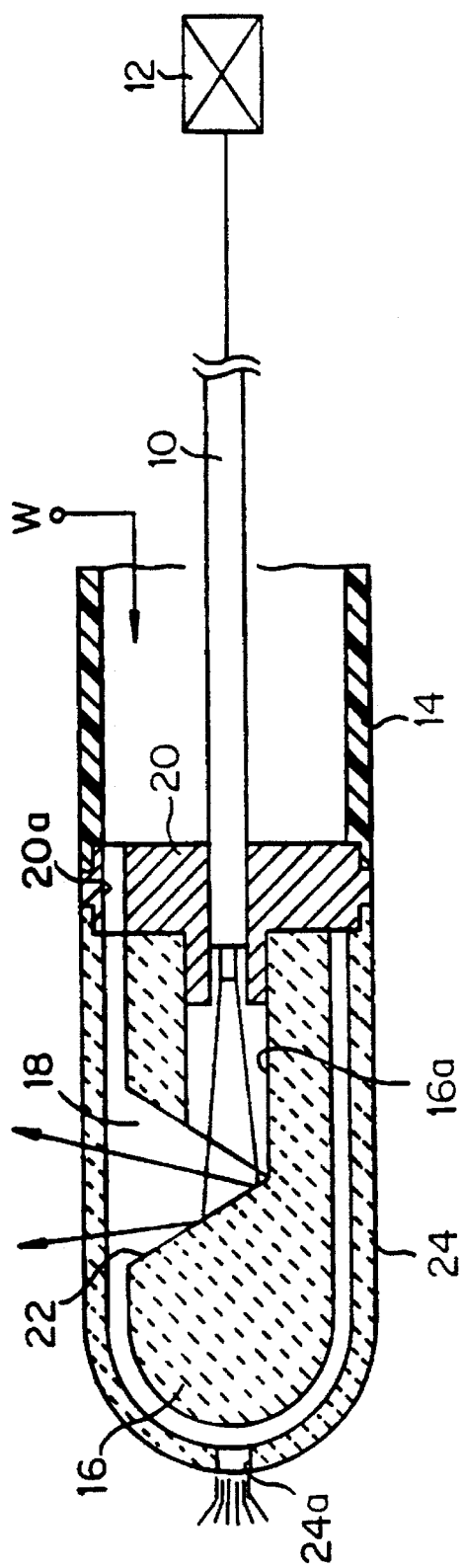
FIG. 1 is a longitudinal sectional view showing a main portion of a laser light irradiation apparatus of the present invention.
FIG. 2 is a perspective view showing a reflector of the apparatus shown in FIG. 1.

Referring now to FIG. 1, there is shown a first embodiment of the present invention. An optical fiber 10 is optically linked with a laser light generator 12. A protection tube 14 made of a plastic tube is provided to surround the optical fiber 10.

A reflector which is represented at 16 may be made of, for example, heat resistant ceramics, heat resistant glass, artificially made sapphire, alumina or metals such as stainless steel. The reflector 16 has an opening 18 on the side thereof as shown in FIG. 2. A through-hole 16a is formed so that it is in communication with the opening 18. A fastener 20 is screwed into the through-hole 16a so that it holds and guides the front end of the optical fiber 10 into the through-hole 16a. The opening 18 of the reflector 16 has an opening angle of 60 in the longitudinal cross section thereof and is formed with a gold plating layer 22 on one side close to the reflector 16.

A covering 24 which is made of, for example, light transparent ceramics such as heat resistant glass is linked with the front end of the protection tube 14 via the metallic fastener 20 to enclose the reflector 16 therein. The covering 24 is formed with a fluid outlet 24a at the front end thereof. Fluid, such as cooling water is supplied into a space between the protection tube 14 and the optical fiber 10. The flange of the fastener 20 is formed with one or more through-holes 20a.

Laser lights from the laser light generator 12 are transmitted through the optical fiber 10 and then emitted from the front end of the optical fiber 10 and are incident upon the gold plating layer 22. The incident lights are reflected by the gold plating layer 22 and pass through the opening 18 and are transmitted through the covering 24 and are incident upon an object of the tissue (not shown) to be irradiated therewith.

During this irradiation process, the cooling water W is continuously supplied to a space within the protection tube 14. The cooling water W flows through the through-holes 20a of the fastener 20 and the space between the reflector 16 and the covering 24 and is continuously discharged from the outlet 24a. As a result of this, even if the laser light irradiation apparatus of the present invention is inserted into a blood vessel, blood would be prevented from flowing into the covering 24. Also even if the apparatus is inserted into the stomach, the gastric juice would be prevented from flowing into the covering 24. Therefore, the space within the covering 24 is constantly kept clean.

On the other hand, since the space in the opening 18 and the through-hole 16a are constantly filled with the cooling water W, a portion facing to the front end of the optical fiber 10, a reflecting surface and the gold plating layer 22 in the embodiment is cooled. This portion would not be damaged by heat due to laser lights even if the power of the laser lights is increased.

Figure 3:
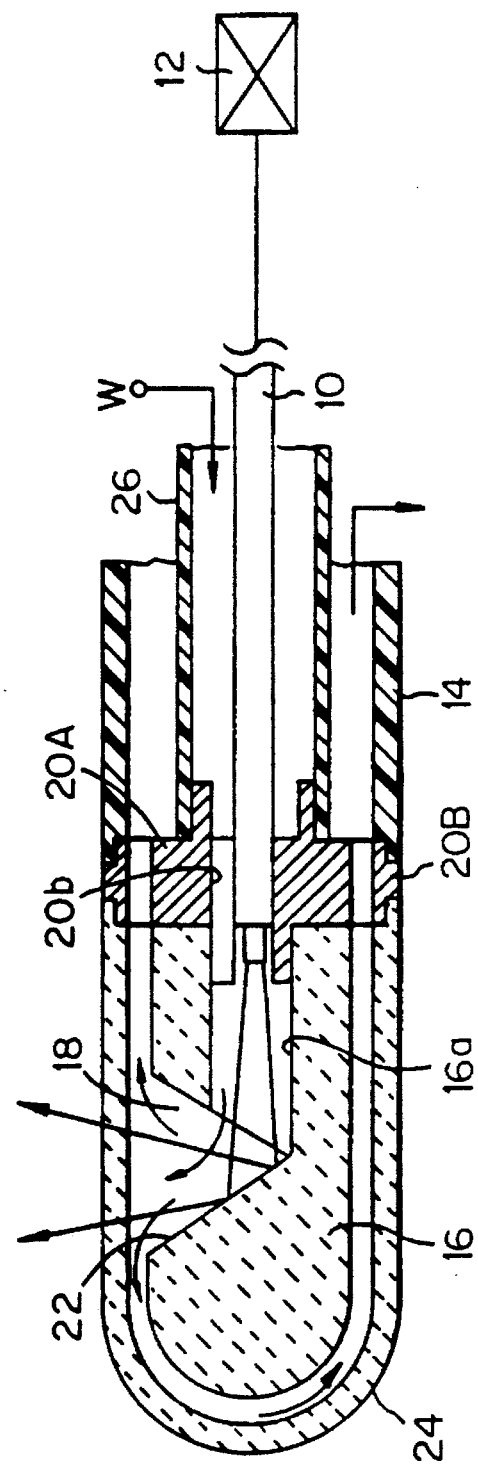
FIG. 3 is a longitudinal sectional view showing a second embodiment of the laser light irradiation apparatus of the present invention.

Referring now to FIG. 3, there is shown a second embodiment of the present invention. The protection tube 14 is linked with the covering 16 by means of a sleeve-like fastener 20B and the reflector 16 is linked with the optical fiber 10 by means of a fastener 20A. The fastener 20A is formed with through-holes 20b. The reflector 24 is linked with a guide tube 26 made of plastic tube so that the tube 26 is in communication with the through-holes 20b.

The cooling water W is also continuously supplied to the space within the guide tube 26 in the irradiation process of the laser light in the second embodiment. The cooling water W passes through-holes 20b of the fastener 20A, then the through-hole 16a and the opening 18. The cooling water then passes through a space between the fastener 20A and the fastener 20b and then a space between the guide tube 26 and the protection tube 14 and is discharged to the outside of the apparatus. The cooling water W is returned or circulated in the second embodiment while the cooling water W is supplied in one-way in the first embodiment.

Since the cooling water W constantly flows through the through-hole 16a and the opening 18 also in the second embodiment, a portion of the front end of the optical fiber 10 positioned in the through-hole 16a and the reflector 16 is prevented from being damaged by the heat due to the laser lights.

Figure 4:
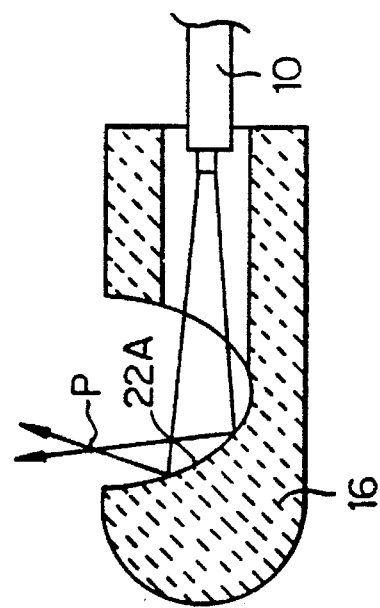
FIG. 4 is a longitudinal sectional view showing a modified reflector.

Referring now to FIG. 4, there is shown an embodiment in which the reflecting surface of the reflector 16 is a concave surface 22A. In case of the concave surface 22A, the energy of the laser lights is concentrated at a point P in the drawing. Accordingly, vaporazation of the tissue can be positively carried out by exposure to the laser lights even if the power of the laser lights is low.

The reflecting surface of the reflector may be made by bonding a thin mirror on the reflector with a bonding agent. If the reflector is made of stainless steel, the reflecting surface may be formed by mirror surface machining the reflector.

Although the apparatus is cooled with the cooling water in the above mentioned embodiments, it may be cooled with a gas such as air or nitrogen gas. The laser lights may be impinged upon the reflecting surface from the front end of the optical fiber via a medium which is capable of transmitting the laser lights therethrough in place of directly impinging upon the reflecting surface from the front end of the optical fiber.

As mentioned above, in accordance with the present invention, invasion of a foreign material such as body liquid or tissue into the irradiation apparatus can be prevented and the laser light emitting end of the optical fiber and the reflecting portion can be cooled so that these portions can be protected from heat due to laser lights. As a result, the optical fiber or reflector can be positively prevented from being damaged even if the laser lights are emitted at a high power.

What is claimed is:

1. A laser light irradiation apparatus for medical treatment by irradiating an object tissue with laser lights transmitted through an optical fiber or fibers, comprising;
    a laser light reflector provided in front of the laser light emitting end of said optical fiber for reflecting the laser light in a lateral direction of the apparatus;
    a covering which covers the reflector and is capable of transmitting the laser light at least at a side portion thereof, said covering being positioned apart from said reflector to form a space completely separating said reflector and said covering; and
    means for continuously supplying fluid to said space between the covering and said reflector; wherein said reflector is linked with the emitting end of the optical fiber by a fastener, said reflector being formed with an opening on a side thereof, said opening having a slanted surface which intersects with the emitted laser light emitted from the optical fiber in the direction of its longitudinal axis.

2. A laser light irradiation apparatus as defined in claim 1 in which said slanted surface of said opening is a surface for reflecting the laser light.

3. A laser light irradiation apparatus as defined in claim 2 in which said slanted surface of said opening is formed with a gold plating surface.

4. A laser light irradiation apparatus for medical treatment by irradiating an object tissue with laser light transmitted through an optical fibber or fibers, comprising:
    a laser light reflector provided in front of the laser light emitting end of said optical fiber for reflecting the laser lights in a lateral direction of the apparatus;
    a covering which covers the reflector and is capable of transmitting the laser light at least at a side portion thereof, said covering being positioned apart from said reflector to form a space completely separating said reflector and said covering;
    means for continuously supplying fluid to said space between the covering and said reflector, and
    a protection tube, separate from the covering, surrounding said optical fiber, said protection tube being linked with said covering by means of a fastener having a through hole, said covering being formed with a fluid outlet through which the supplied fluid having passed through said through hole and said protection tube can be discharged.

5. A laser light irradiation apparatus for medical treatment by irradiating an object tissue with laser lights transmitted through an optical fiber or fibers, comprising:
    a laser light reflector provided in front of the laser light emitting end of said optical fiber for reflecting the laser light in a lateral direction of the apparatus;
    a covering which covers the reflector and is capable of transmitting the laser light at least at a side portion thereof, said covering being positioned apart from said reflector to form a space completely separating said reflector and said covering; and
    means for continuously supplying fluid to said space between said covering and said reflector; wherein said reflector is linked with the emitting end of the optical fiber, said reflector being formed with an opening on a side thereof, said opening having a slanted surface which intersects with the laser light emitting from the emitting end of the optical fiber;
    a guide tube surrounding said optical fiber, a protection tube being provided surrounding the guide tube;

said reflector being linked to said guide tube by a fastener having a through hole throughout which the laser light emitted from the front end of the optical fiber is transmitted in the direction of its longitudinal axis, said through hole being in communication with said guide tube; in which said fluid is supplied into said guide tube and passes through said through hole, said opening and then is discharged the outside of the apparatus after passing through a space between said guide tube and said protection tube.

* * * * *